(12) United States Patent
Ronlan

(10) Patent No.: US 6,500,465 B1
(45) Date of Patent: Dec. 31, 2002

(54) DISINFECTING AND SPOROCIDAL COMPOSITION AND PROCESS FOR DECONTAMINATING BUILDINGS

(76) Inventor: Alvin Ronlan, 3414 Norfolk St., Pompano Beach, FL (US) 33062

( * ) Notice: Subject to any disclaimer, the term of this patent is extended or adjusted under 35 U.S.C. 154(b) by 0 days.

(21) Appl. No.: 10/086,822

(22) Filed: Mar. 4, 2002

(51) Int. Cl.$^7$ .................. A01N 59/00; A01N 25/22; A01N 31/02; A61L 2/22; A61L 9/015
(52) U.S. Cl. .............. 424/616; 424/613; 424/76.2; 424/76.8; 514/642; 514/643; 514/714; 514/957; 514/970; 422/4; 422/5; 422/27; 422/28; 422/120
(58) Field of Search ................ 424/616, 613, 424/76.2, 76.8, 43; 514/642, 643, 714, 957, 970; 422/4, 5, 27, 28, 120

(56) References Cited

U.S. PATENT DOCUMENTS

| 3,645,840 A | * | 2/1972 | Lincoln et al. ............... 162/78 |
| 4,169,123 A | * | 9/1979 | Moore et al. .................. 422/29 |
| 4,518,585 A | * | 5/1985 | Greene et al. ............... 424/616 |
| 4,952,370 A | * | 8/1990 | Cummings et al. ............ 422/28 |
| 5,147,884 A | * | 9/1992 | Diehl et al. .................. 514/365 |
| 5,284,597 A | * | 2/1994 | Rees ........................... 510/280 |
| 6,096,265 A | * | 8/2000 | Mezger et al. ................. 422/28 |
| 6,406,666 B1 | * | 6/2002 | Cicha et al. .................... 422/28 |

OTHER PUBLICATIONS

Block, Seymour S. Disinfection, Sterilization and Preservation. Lea & Febiger, Philadelphia, pp. 167–172, 1991.*

* cited by examiner

Primary Examiner—John Pak

(57) ABSTRACT

The present invention relates to a volatile, residue free peroxide antimicrobial composition, which can be applied as a penetrating and durable, fine aerosol, that has superior strength with respect to decontaminating buildings infected with bacteria, fungi, virus or fungal or bacterial spores.

The present invention is also directed to a process for decontaminating large man made structures and the air contained in these.

9 Claims, No Drawings

DISINFECTING AND SPOROCIDAL COMPOSITION AND PROCESS FOR DECONTAMINATING BUILDINGS

TECHNICAL FIELD

The present invention relates to a volatile, residue free peroxide antimicrobial composition, which can be applied as a penetrating and durable, fine aerosol, that has superior strength with respect to decontaminating buildings infected with bacteria, fungi, virus or fungal or bacterial spores.

The present invention is also directed to a process for decontaminating large man made structures and the air contained in these.

BACKGROUND OF THE INVENTION

Disinfecting biologically contaminated large man-made structures—as for example shopping malls, sports complexes, high rises, subway systems, factories, etc.—as well as the air contained in these structures is an extremely challenging undertaking and none of the presently available methods are satisfactory.

The most widely used method is fumigation with formaldehyde. Formaldehyde is a suspected carcinogenic and a potent allergen which, due to inevitable residues left after a treatment, severely limits its usefulness in structures inhabited by man.

Numerous attempts have been made to use oxidizing gases such as ozone or chlorine dioxide for decontaminating large buildings. However, the results have invariably been very disappointing. This is to some extent due to the inherent inability of gases to penetrate a porous structure within a reasonable time. In fine pores diffusion is the only way for a gas to spread, and this process is slow. Mainly, though, the failure of ozone and chlorine dioxide in building decontamination is due to the instability and extreme reactivity of these gases. They are very toxic to man and will also corrode virtually any oxidizeable material, (metals, wood, textiles, plants, plastics, etc.) Actually the major part of these gases will be consumed in unwanted oxidation reactions, that cause collateral damage, and for health and safety reasons is basically not possible to apply these gases at the levels required for efficient decontamination to take place.

From a health and environmental point of view disinfecting agents based on peroxides, such as hydrogen peroxide, peracetic acid and like, is much to be preferred. Their oxidizing strength, without being excessive, in principle is adequate for killing virtually all microbes. Unfortunately hydrogen peroxide or other peroxides are too unstable and hazardous to allow fumigating with their vapors.

High density, fine aerosols (aerosol droplet diameter less than 50 micron) of aqueous peracetic acid, hydrogen peroxide or combinations thereof, suitable for disinfecting are only sufficiently stable at 100% R.H., and the commercial fog-disinfecting methods using peroxides are only suitable for confined spaces where all materials and equipment are corrosion resistant or protected.

SUMMARY DISCLOSURE OF INVENTION

The objective of said invention is to provide an antimicrobial composition that can be applied at ambient conditions as a high density, durable fine aerosol having superior disinfecting strength with respect to microbes and spores thereof adhered to inanimate surfaces as well as with respect to airborne microbes and microbial spores, such an aerosol being imminently suitable for emergency decontamination of buildings and spaces infected with hazardous microbes or spores thereof.

As a result of extensive research, I have found that a mixture of hydrogen peroxide and tert-butyl hydroperoxide in propylene glycol or other water compatible glycols can be converted to a high density, durable fine aerosol, using conventional thermofogging equipment (see below), without appreciable loss of peroxide activity through thermal decomposition, and that such aerosols manifest unexpected high disinfecting strength with respect to microorganisms including fungal and bacterial spores without causing staining, corrosion or irritating odors. The use of a combination of hydrogen peroxide and tert-butyl hydroperoxide for bleaching of pulp has been described in U.S. Pat. No. 3,645,840. However, it is by no means obvious how the disclosures of U.S. Pat. No. 3,645,840 can be applied to an aerosol process for disinfecting buildings. U.S. Pat. No. 5,147,884 describes antimicrobial composition containing tert-butyl hydroperoxide and a monophenylglycol ether.

In the disinfecting method according to this invention the peroxide antimicrobial agent is converted into a fine aerosol using various types of "thermofoggers", such as for example a pulsejet fogger or an electrical fogger with a flash heating system. Examples of pulsejet thermofoggers are "Patriot" and "Black Hawk" manufactured by Curtis Dynafog Corporation, Ltd., Indianapolis, and an example of a suitable electrical thermofogger is "Fogmax" manufactured by CITC, Lynnwood, Wash. Normally the high temperature in thermofoggers will destroy any peroxide. However, as mentioned above, I have discovered combinations of peroxides and carriers that can resist the high temperatures encountered in thermofoggers, making this ideal aerosol technique available to generate fine, high density, durable aerosols of peroxides. The fine aerosol produced in this manner will spread much like a gas, which makes it ideal for decontamination of large structures as well as inaccessible areas of buildings. However, in contrast to a gaseous agent, once an aerosol according to this invention has settled on a surface, it behaves like a liquid, that is, the agent can be transported by capillary action deep into a porous material, which is impossible with ozone or chlorine dioxide. The peroxide disinfecting method according to this invention kills mold, bacteria and fungi as well as spores thereof. The same oxidation reaction also degrades it and neutralizes the odor compounds from mold, fungi and bacteria (MVOC).

Another advantage of the disinfecting method according to this invention is that airborne microbes are disinfected with the same efficiency as those adhered to surfaces. Furthermore airborne particulate matter is removed from treated air spaces through agglomeration with the aerosol droplets, leaving the treated air virtually free from microbes and their spores.

The present invention provides a safe and effective method of sanitizing surfaces and ambient air by removing, reducing or retarding the growth of pathogenic microorganisms and molds without the use of substances that are toxic to humans and without leaving any permanent residue.

BEST MODE FOR CARRYING OUT THE INVENTION

As the peroxide used as component (A) of said invention, commercially available hydrogen peroxide aqueous solutions can be used favorably.

Next, the volatile, organic peroxide used as component (B), is commercially available t-butyl hydroperoxide.

The content of the hydrogen peroxide used as component (A) in the biocidal composition is generally 0.5–60 wt %, preferably 0.5–30 wt %, and more preferably 0.5–20 wt %. For practicality, 3–20 wt % is most favorable. The content of t-butyl hydroperoxide, which is component (B), is 0.5–60 wt %, preferably 0.5–30 wt %, and more preferably 0.5–10 wt %. For practicality, 3–10 wt % is most favorable.

If component (A) or (B) is lower than said range, the disinfecting action is low, when component (A) or (B) is greater than said range, the product becomes difficult to handle as a biocidal composition.

The solvent carrier (C) of the biocidal composition in said invention is important for thermal stability, for aerosol forming properties as well as for obtaining high disinfecting strength. After extensive research I have found that mixtures of water and a low volatile, water compatible glycol or glycol ether are preferable, and most preferable are mixtures of propylene glycol and water where the content of propylene glycol in water is 10–90 wt %.

The biocidal composition of the present invention is normally manufactured by dissolving hydrogen peroxide (A) and t-butyl hydroperoxide (B) in a mixture of water and propylene glycol (C). The content of propylene glycol (C) used in the biocidal composition in said invention is selected from a range of 5–99 wt %, preferably 50–95 wt %, and more preferably 60–90 wt %.

In the biocidal composition of the present invention, it is preferable to add a surfactant. As the surfactant, cationic surfactants such as aryl-alkyl or dialkyl dimethyl ammonium halides, nonionic surfactant such as polyoxyethylene alkyl ethers, polyoxyethylene fatty acid esters, amine oxides, etc., and anionic surfactants such as soaps, alkyl sulfates, and alkylbenzenesulfonates, etc., can be utilized. It is preferable for the quantity of the surfactant added to be 0.1–10 wt % in the biocidal composition. By the addition of a surfactant, it is possible to assist in the penetration of the biocidal composition with respect to the bacterial bio-film, mold or spore coating and to enhance the biocidal effect.

The biocidal composition of the present invention is applied as a fine aerosol using thermofogging equipment described above, and it is possible to disinfect spores, bacterial bio-films or molds effectively by contacting with said fine aerosol.

By thermal fogging, the biocidal composition of this invention is dispersed in 10–20 micron particle sizes and the treated building is kept closed for a minimum of twenty-four (24) hours for treatment to occur.

No rinsing of treated surfaces is required after or prior to application of the disinfecting aerosol according to this invention.

Typical bacteria which can be disinfected with the composition of this invention include: *staphylococcus aureus, staphylococcus pyogenes, streptococcus hemolyticus, streptococcus dysgalactiae, mycobacterium tuberculosis, salmonella typhosa, salmonella typhimurium, salmonella pullorum, hemophilus parasuis, clostridium perfringens, mycoplasma synoviae, mycoplasma hyopneumoniae, pasteurella multocida, klebsiella pneumoniae, staphylococcus epidermis, streptococcus agalactiae, streptococcus fecalis, listeria monocytogenis, mycobacterium tuberculosis, salmonella choleraesuis, salmonella enteritidis, pseudomonas aeruginosa, clostridium tetani, diplococcus pneumoniae, mycoplasma gallisepticum, escherichia coli, pasteurella hemolytica, alcaligenes faecalis, salmonella gallinarum, salmonella arizonae, salmonella schotimuelleri, staphylococcus hyicus, streptococcus pyogenes, haemophilus parasuis;* and, *bordetella bronchiseptica.*

Fungus types, which may be disinfected by the composition of this invention, include: *aspergillus fumigatus, aspergillus glacus, aspergillus nidulans, aspergillus flavus, aspergillus niger, fusarium solani;* and penicillium variable.

Spore types, which may be disinfected by the composition of this invention, include: *Bacillus anthracis,* B., and (bacterial spores) and Stachybotrys, Aspergillus, Penicillium, Trichoderma and Alternaria spp. (fungal spores).

Viruses which are disinfected by this composition include: Adenoviridae (Egg Drop Syndrome), Herpetoviridae (Infectious Bovine), Rhinotracheitis (Aujeszky's Disease), Feline Herpes, Iridoviridae (African Swine Fever), Parvoviridae, (Canine Parvovirus), Poxviridae Pseudo (Cowpox), Coronaviridae (Transmissible Gastro-Enteritis), Avian Infectious Bronchitis, Canine Coronavirus, Orthomyxoviridae (Avian Influenza), Paramyxoviridae (Newcastle Disease), Distemper, Picornaviridae (Swine Vesicular Disease), Foot & Mouth Disease, Reoviridae Gumboro (IBD), Retroviridae (Maedi & Visna), AIDS.

TABLE 1

THERMOFOGGING STABILITY OF PEROXIDE FORMULATIONS

| COMPONENT | 14% FORMULATION | | | | | | 17% FORMULTION | | | 10% FORMULTION | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| HYDROGEN PEROXIDE, wt % | 14 | 0 | 7 | 7 | 11 | 3 | 17 | 0 | 10 | 10 | 10 | 0 | 6 | 6 |
| t-BUTYL HYDROPEROXIDE, wt % | 0 | 14 | 7 | 7 | 3 | 11 | 0 | 17 | 7 | 7 | 0 | 10 | 4 | 4 |
| PROPYLENE GLYCOL, wt % | 70 | 70 | 70 | 70 | 70 | 70 | 70 | 70 | 70 | 70 | 70 | 70 | 70 | 70 |
| DIDECYL DIMETHYL AMMONIUM Cl | 0 | 0 | 0 | 1 | 0 | 0 | 0 | 0 | 0 | 1 | 0 | 0 | 0 | 1 |
| WATER, wt % | 16 | 16 | 16 | 15 | 16 | 16 | 13 | 13 | 13 | 12 | 20 | 20 | 20 | 19 |
| % RELATIVE LOSS OF PEROXIDE BY THERMOFOGGING | 50 | 0 R | 6 | 4 | 20 | 0 | 59 | 0 R | 8 | 6 | 43 | 0 R | 3 | 1 |

Evaluation of Thermofogging Stability of Various Peroxide Formulations

The stability of the peroxide disinfectants according to this invention were determined in the following manner:

Absolute measurement of the peroxide degradition in the thermofogging process is very difficult due to the uncontrolled evaporation/condensation processes taking place during and after aerosolization. For our purpose a relative measurement is suffucient. Three series of measurements were carried out with varying total amount of peroxide (14%, 17% and 10%) and constant amount of propylene glycol carrier (Table 1). The formulation Examples of Table 1 were loaded into the chemical tank of a pulsejet thermofogger (Patriot from Curtis Dynafog Corp.) and dispensed as a fine aerosol (10–20 micron droplet size) into a 15 $m^3$ cylindrical (diameter 2 m and length 5 m) test chamber in which 3 clean, tared glass petri dishes (diameter 20 cm) had been placed on the bottom. An amount of aerosol corresponding to approximately 2 g of peroxide per $m^2$ was dispensed. The aerosol was allowed to settle for 30 minutes before the petri dished were taken out of the chamber. Each dish was weighed and then rinsed with a total of 50 ml of destined water and the peroxide content in this extract was determined by titration with thiosulfate. In each series the value measured for the formulation based on tert-butyl hydroperoxide alone was taken as the relative value of 0% degradation of peroxide (R). As can be seen from Table 1, t-butyl hydroperoxide substantially reduces the thermal decomposition of hydrogen peroxide in the thermofogging process. This stabilizing effect of t-butyl hydroperoxide on hydrogen peroxide is even more pronounced when an electrical fogger is used for aerosol generation.

TABLE 2

APPLICATION EXAMPLES

| COMPONENT, WT% | EXAMPLE No. 1 | 2 | 3 | 4 |
|---|---|---|---|---|
| HYDROGEN PEROXIDE | 14 | 0 | 7 | 7 |
| t-BUTYL HYDROPEROXIDE | 0 | 14 | 7 | 7 |
| PROPYLENE GLYCOL | 70 | 70 | 70 | 70 |
| DIDECYL DIMETHYL AMMONIUM CHLORIDE | 0 | 0 | 0 | 1 |
| WATER | 16 | 16 | 16 | 15 |

Evaluation of Antimicrobial Efficacy

The exemplary formulations described in Table 2 above were evaluated for their antimicrobial efficacy against *Pseudomonas aeruginosa* (ATCC 15442), *Escherichia coli* (ATCC 10536), *Staphylococcus aureus* (gram-positive type pathogenic bacteria) (ATCC 6538), *Enterococcus hirae* (ATCC 10541), *Salmonella typhimurium* (gram-negative type pathogenic bacteria) (ATCC 13311), *Aureobasidium pullulans* (black mold) in the following manner:

Culture Method:

The test organisms described above were transplanted individually to suitable agar culture media and incubated (at 30–35° C. and 24 hours for the bacteria cultures and 28–30° C. and 20 days for the mold culture) to develop confluent growth, and the bacterical (mold) colonies forming units (cfu) was determined (no treatment level).

Treatment Method:

Two Petri dishes of each culture were placed in a chamber with controlled temperature (25° C.) and humidity (85% R.H.). The chamber was filled with an aerosol (average droplet size 10 micron) of the exemplary formulation (Table 2) to be tested using a pulse-jet fogger (Curtis Dynafog model Patriot). The amount of formulation applied in all cases corresponded to approximately 20 g of formulation per square meter culture medium. The chamber was kept closed for 24 hours and the bacterial and mold cfu were determined.

Method for Evaluation of the Biocidal Activity:

The test method for evaluation of the bactericidal activity of a composition on clean surfaces described in European Standard, EN 1276:1997 issued by the European committee for standardization, Brussels, was adapted to this test.

European Standard, EN 1276:1997, specifies a test method and requirements for the minimum bactericidal activity of a disinfecting composition. The test is passed if the bacterial colonies forming units (cfu) are reduced from a $10^7$ cfu (initial level) to a $10^2$ cfu (final level after contact with the disinfecting product), i.e. a $10^5$ reduction of the viability is necessary. The results obtained for the exemplary compositions in Table 2 are shown in Table 3. "+" indicates at least a 5 log reduction in cfu and "−" indicates less than a 5 log reduction in cfu

TABLE 3

EVALUATION OF BIOCIDAL EFFICACY

| TEST ORGANISM | EXAMPLE BIOCIDAL EFFICACY 1 | 2 | 3 | 4 |
|---|---|---|---|---|
| *Staphylococcus aureus* (ATCC 6538) | + | − | + | + |
| *Salmonella cholerasuis* (ATCC 10708) | + | − | + | + |
| *Pseudomonas aeruginosa* (ATCC 15442) | − | − | + | + |
| *Aureobasidium pullulans* | − | − | + | + |
| *Aspergillus flavus* | − | − | + | + |
| *Penicillium sp.* | − | − | + | + |

Evaluation of Sporocidal Efficacy

The exemplary formulations described in Table 2 above were evaluated for their sporocidal efficacy against *Bacillus globigii, B. licheniformis* and *B. subtilis* spores (bacterial spores) and against spores of Aspergillus and Penicillium spp.

Contamination Simulation Method:

A glass contamination chamber with a floor surface area of 0.215 $m^2$ was placed into a fume hood and outfitted with a HEPA-filtered ventilation port to relieve excess air during the contamination process. An aerosol nebulizer was mounted on the interior cover at one end of the chamber. Various pieces of optical scanning equipment and several control petri dishes were placed onto the floor of the chamber. Two milliliters of a $3.0\times10^9$ CFU/mL spore preparation diluted with 3 mL of sterile $ddH_2O$ were added to the reservoir of the aerosol nebulizer. The chamber was sealed and compressed air was fed into the nebulizer to begin the contamination process, which lasted approximately 15 minutes. Once the contents of the reservoir were completely disseminated, a small amount of clean air was allowed to vent through the nebulizer and into the chamber overnight to remove excess moisture. The next morning, half of the petri dishes were removed to serve as controls for the determination of contamination density. Additionally, selected areas of the test equipment that were fully exposed to the Bacillus/Aspergillus/Penicillium dissemination were swabbed to collect and measure viable spores. The equipment and the remaining petri dishes were then transferred into the large (8 $m^3$) chamber and placed onto a table in the same orientation as used in the contamination chamber.

Decontamination Method:

Immediately following transfer of the test samples, the chamber was filled with an aerosol (average droplet size 15 micron) of the exemplary formulation (Table 2) to be tested using a pulse-jet fogger (Curtis Dynafog model Patriot). The amount of formulation applied in all cases corresponded to approximately 20 g of formulation per square meter of test surface. The chamber was kept closed for 24 hours whereafter the remaining control petri dishes were removed and the surfaces of the test equipment were swabbed. All samples were prepared and cultured to determine the number of surviving spores.

Analysis/Method for Evaluation of the Sporocidal Activity:Spores were extracted from the control samples by adding 5 mL of sterile ddH$_2$O to each plate and thoroughly swabbing the plate with a cotton swab to release the adsorbed spores. Serial dilutions were performed on each extract from the control plates to achieve 1:1000, 1:10,000 and 1:100,000 dilutions respectively. A 100 mL aliquot of each control plate dilution ($10^{-3}$, $10^{-4}$, and $10^{-5}$) was plated in triplicate on tryptic soy agar. For the test equipment samples, each swab was wetted in 100 mL of ddH$_2$O and used to swab the selected surface(s). The swab tips were clipped into centrifuge tubes where an additional 1.0 mL of ddH$_2$O was added. These extracts were serially diluted to yield $10^{-2}$, $10^{-3}$, and $10^{-4}$ dilutions respectively. A 100 mL aliquot of each dilution level was plated in triplicate and incubated overnight at 37° C.

The control petri dishes were extracted and plated in triplicate to generate data using the standard test procedure.

The test is passed if the bacterial colonies forming units (cfu) are reduced from a $10^6$ cfu/cm$^2$ (initial level) to a $10^1$ cfu/cm$^2$ (final level after contact with the disinfecting product), i.e. a $10^5$ reduction of the viability is necessary. The results obtained for the exemplary compositions in Table 2 are shown in Table 4. "+" indicates at least a 5 log reduction in viable spore cfu and "−" indicates less than a 5 log reduction in cfu

TABLE 4

EVALUATION OF SPOROCIDAL EFFICACY

| TEST ORGANISM | EXAMPLE/BIOCIDAL EFFICACY | | | |
|---|---|---|---|---|
| | 1 | 2 | 3 | 4 |
| Bacillus globigii spores | − | − | + | + |
| Bacillus licheniformis spores | − | − | + | + |
| Bacillus subtilis spores | − | − | + | + |
| Aspergilius spp. spores | − | − | + | + |
| Penicillium spp. spores | − | − | + | + |

Evaluation of Odor Removal Efficacy

Odor Testing Method 10 panelists smelled the odor of the various culture dishes described above before and after the treatment with the compositions of Table 2.

The odor was evaluated as follows:
+: Most or all panelists do not sense an irritating or bad odor.
0: About half of the panelists sense an irritating or bad odor.
−: Most or all panelists sense an irritating or bad odor.

TABLE 5

EVALUATION OF ODOR REMOVAL EFFICACY.

| TEST ORGANISM | EXAMPLE/ODOR REMOVAL EFFICACY | | | |
|---|---|---|---|---|
| | 1 | 2 | 3 | 4 |
| Staphylococcus aureus (ATCC 6538) | + | + | + | + |
| Salmonella cholerasuis (ATCC 10708) | + | 0 | + | + |
| Pseudomonas aeruginosa (ATCC 15442) | + | + | + | + |
| Aureobasidium pullulans | 0 | − | + | + |
| Aspergilius flavus | 0 | 0 | + | + |
| Penicillium sp. | 0 | 0 | + | + |

Evaluation of Mycotoxin Denaturing Efficacy

This evaluation was carried out using pieces of gypsum board from a water damaged home infested with *Stachybotrys chartarum*. This species of mold produces macrocyclic trichothecene mycotoxins such as Verrucarin, Roridin and Satratoxin. Some symptoms germane to exposure to this mold include: cold/flu symptoms, nose bleeds, burning sensation, coughing or difficulty breathing, sore throat, diarrhea, headaches, dizziness, nausea, fatigue, and rash at the point of contact—especially in areas of heavy perspiration. These mycotoxins can also affect the appetite center of the brain, often reducing the appetite of exposed individuals. The presence of trichothecene mycotoxins was established using a so called Enzyme Linked Immunosorbant Assay (ELISA, based on a coupling reaction between a specific mycotoxin and antibodies specific for those mycotoxin). No attempts were made to make a quantitative determination. A positive assay indicates a mycotoxin level above 100 parts per billion (0.1 ppm).

Two pieces (100 cm2 each) of mold infested gypsum board was treated each of the exemplary compositions of Table 2 in the manner described under "Treatment Method" above. The results are shown in Table 6. "+" indicates no detection of mycotoxins, and "−" that presence of mycotoxins was detected.

TABLE 6

EVALUATION OF MYCOTOXIN DENATURING EFFICACY

| TEST ORGANISM | EXAMPLE/MYCOTOXIN DENATURING EFFICACY | | | |
|---|---|---|---|---|
| | 1 | 2 | 3 | 4 |
| Stachybotrys chartarum | − | − | + | + |

Tests have been carried out to establish the virucidal activity of two of the above composition (3 and 4 in Table 2) in accordance with the standard test procedures. These tests have shown the effectiveness of the composition against the following broad spectrum of viruses and viral infections when applied as described under "Treatment Method" above, which gave a 4 log reduction in virus titre:

Adenoviridae (Egg Drop Syndrome), Herpetoviridae (Infectious Bovine), Rhinotracheitis (Aujeszky's Disease), Feline Herpes, Iridoviridae (African Swine Fever), Parvoviridae, (Canine Parvovirus), Poxviridae Pseudo (Cowpox), Coronaviridae (Transmissible Gastro-Enteritis), Avian Infectious Bronchitis, Canine Coronavirus, Orthomyxoviridae (Avian Influenza), Paramyxoviridae (Newcastle Disease), Distemper, Picornaviridae (Swine Vesicular Disease), Foot & Mouth Disease, Reoviridae Gumboro (IBD), Retroviridae (Maedi & Visna), AIDS.

From the foregoing, it is to be understood that the compositions according to the invention provide excellent and surprising disinfecting and deodorant benefits to hard surfaces. Such compositions in accordance with the present inventive teaching are particularly advantageously used against known pathogenic/nuisance microorganisms commonly found in indoor environments.

While the invention is susceptible of various modifications and alternative forms, it is to be understood that specific embodiments thereof have been shown by way of examples which however are not intended to limit the invention to the particular forms disclosed; on the contrary the intention is to cover all modifications, equivalents and alternatives falling within the scope and spirit of the invention as expressed in the appended claims.

I claim:

1. A liquid biocidal, deodorant and mycotoxin and/or endotoxin denaturing composition, comprising:

(a) 0.5–60 wt % of hydrogen peroxide;
(b) 0.5–60 wt % of t-butyl hydroperoxide;
(c) 5–90 wt % of a water compatible glycol or glycol ether; and
(d) 0–89 wt % of water.
   said composition being characterized by its lack of residue and being convertible, utilizing thermofogging techniques, into a durable, high density, fine aerosol with effective antimicrobial, deodorizing and toxin denaturing activity.

2. A composition according to claim 1, wherein the molar ratio between hydrogen peroxide and t-butyl hydroperoxide is between 1:10 and 10:1 and the total peroxide concentration is between 0.5 and 30% by weight.

3. A composition according to claim 2, wherein the molar ratio between hydrogen peroxide and t-butyl hydroperoxide is between 1:3 and 3:1 and the total peroxide concentration is between 5 and 20% by weight.

4. A composition according to claim 1 where the glycol is propylene glycol and the total propylene glycol concentration is between 10 and 90% by weight.

5. A composition according to claim 4 where the propylene glycol concentration is between 20 and 70% by weight.

6. A composition according to claim 1, which additionally includes up to 10% by weight of a surfactant.

7. A composition according to claim 4, wherein the surfactant is a quaternary ammonium compound.

8. A composition according to claim 7, wherein the surfactant is didecyl dimethyl ammonium chloride.

9. A method of disinfecting and deodorizing and/or denaturing myco- and/or endotoxins which comprises applying an antimicrobially effective amount of the solution claimed in claim 1 in the form of a durable, high density, fine aerosol to a surface, object or air space requiring disinfecting and/or deodorizing and/or myco- and/or endotoxin denaturing.

* * * * *